(12) United States Patent
Lovoi et al.

(10) Patent No.: US 6,989,486 B2
(45) Date of Patent: Jan. 24, 2006

(54) HIGH VOLTAGE CABLE FOR A MINIATURE X-RAY TUBE

(75) Inventors: Paul A. Lovoi, Saratoga, CA (US); Peter C. Smith, Half Moon Bay, CA (US); Alex Lim, Santa Clara, CA (US)

(73) Assignee: Xoft microTube, Inc., Fremont, CA (US)

( * ) Notice: Subject to any disclaimer, the term of this patent is extended or adjusted under 35 U.S.C. 154(b) by 0 days.

(21) Appl. No.: 10/961,962

(22) Filed: Oct. 8, 2004

(65) Prior Publication Data

US 2005/0061533 A1    Mar. 24, 2005

Related U.S. Application Data

(63) Continuation-in-part of application No. 10/397,498, filed on Mar. 26, 2003.

(51) Int. Cl.
  *H01B 7/34*  (2006.01)
  *H01B 7/00*  (2006.01)
(52) U.S. Cl. .................. 174/28; 174/110 R; 174/113 R
(58) Field of Classification Search .................. 174/36, 174/102 R, 103, 105 R, 105 SC, 106 R, 174/106 SC, 108, 110 R, 113 R, 117 F, 117 FF, 174/120 R, 120 SC
See application file for complete search history.

(56) References Cited

U.S. PATENT DOCUMENTS

| 3,142,721 A | * | 7/1964 | Long ..................... 174/65 R |
| 3,586,751 A | * | 6/1971 | Schoerner ................ 174/115 |
| 3,982,059 A | * | 9/1976 | Holland et al. ........... 174/73.1 |
| 4,382,653 A | * | 5/1983 | Blanchard ................ 439/610 |
| 4,398,058 A | * | 8/1983 | Gerth et al. ............. 174/106 D |
| 4,684,766 A | * | 8/1987 | Tanaka et al. ............. 174/115 |
| 4,964,148 A | * | 10/1990 | Klostermann et al. ...... 378/127 |
| 5,109,599 A | * | 5/1992 | Ohlhaber ................... 29/828 |
| 5,154,638 A | * | 10/1992 | Sireul et al. .............. 439/611 |
| 5,310,361 A | * | 5/1994 | Muchowicz et al. ........ 439/610 |
| 5,596,621 A | * | 1/1997 | Schwarz et al. ........... 378/130 |
| 5,846,355 A | * | 12/1998 | Spencer et al. ............. 156/53 |
| 6,134,300 A | * | 10/2000 | Trebes et al. .............. 378/136 |
| 6,324,257 B1 | * | 11/2001 | Halavee ................... 378/121 |
| 6,362,415 B1 | * | 3/2002 | Snyder et al. ............ 174/15.1 |
| 6,438,206 B1 | * | 8/2002 | Shinar et al. ............. 378/123 |
| 6,452,102 B1 | * | 9/2002 | DeForest et al. ......... 174/75 C |
| 6,677,534 B2 | * | 1/2004 | Yamamoto et al. ..... 174/113 R |

(Continued)

Primary Examiner—William H. Mayo, III
(74) Attorney, Agent, or Firm—Thomas M. Freiburger (57) ABSTRACT

In a miniature x-ray tube, which may be on the order of approximately 1 mm in diameter or even less, a high voltage cable is provided in various embodiments for conducting current to the cathode of the x-ray tube and for conducting high voltage to the cathode and anode of the tube. In various embodiments of the cable, two conductors occupy a center region of the cable, packed as closely together as possible, in various shapes that are compact and present as smooth as possible an external shape for maximizing dielectric properties against the exterior high voltage ground, surrounding and generally concentric with the inner conductors. The inner conductors, which carry high voltage in opposition to the outer ground, can be in opposed D shapes, coaxial, two flattened conductors side by side, or simply a pair of cylindrical wires positioned as closely as possible. The space between the inner conductors and the outer ground can be occupied by a glass insulator, polymer, successive layers of polymers and adhesive, air, gas, vacuum or other dielectrics. A partially conductive region can surround the inner conductors.

45 Claims, 3 Drawing Sheets

U.S. PATENT DOCUMENTS 6,781,060 B2 * 8/2004 Radley .................... 174/84 R 2002/0063500 A1 * 5/2002 Keren ........................ 313/30

* cited by examiner

HIGH VOLTAGE CABLE FOR A MINIATURE X-RAY TUBE

BACKGROUND OF THE INVENTION

This application is a continuation in part of application Ser. No. 10/397,498, filed Mar. 26, 2003.

This invention concerns the composition, structure and fabrication of a high voltage cable that leads to and is connected to a miniature x-ray source, for applications including post-operative radiation of breast tissue and treatment within various lumens of the human body, including blood vessels.

Miniature or small x-ray tubes for human therapeutic treatment are discussed in several prior patents, including U.S. Pat. Nos. 5,854,822, 5,621,780 and 6,319,188, as well as co-pending application Ser. No. 10/397,498, commonly owned with this application. Such small x-rays tubes have been proposed or developed for the purpose of treating tumors within surgical openings in the body, for treatment within blood vessels using a catheter that contains the tube, and for other radiation treatments within the body. The cited pending application describes a cathode assembly with a cathode manufactured by MEMS technology and discloses a means of forming an extractor cup and electrically connecting the extractor cup to high voltage. The application also discloses several configurations for the high voltage cable of the device, which also carries cathode heating current on multiple inner conductors, in configurations that maximize dielectric properties to prevent arcing to a ground at an outer position on the cable. The application discloses several embodiments, and shows a form of connection of the cable to the cathode end of an x-ray tube.

The x-ray tube potential contemplated for such miniature x-ray devices is greater than 25 kV, and preferably greater than 40 kV and may be 50 kV or greater. The insulation and components in the cable, which must be quite flexible and small in diameter, preferably smaller than the x-ray tube, are required to withstand very high dielectric fields. Effective insulating material must surround and encapsulate the high voltage interior conductors, insulating them from the exterior ground. Providing enough insulating protection within a very small profile, so as to prevent arcing and cable failure, is a challenge. Placing as much insulating protection in as small a profile as possible must be achieved, while lowering the field gradient as much as possible. Such a challenge involving high voltage and extremely small size has not previously been undertaken, because the typical HV cable situation has involved much larger size or much lower voltages. Materials and design are critical, and become much more critical with reductions in size, to the order of about 1 mm external diameter, often with a requirement to pass through tight radius curves.

High voltage is divided along any path between conductors at different potentials whether or not there is a gas, solid or liquid between the conductors. The division of voltage can be proportional to the distance (linear division) or some other distribution. If the distribution is not linear, there will be a place where the voltage gradient is higher than the average linear gradient. This distribution can change with time as well as due to breakdown and material damage. When the distribution is higher than the dielectric being used can support an arc can occur.

If a solid insulator is used as the dielectric, it is normally very high resistance material. The voltage divides between the conductors based mostly on capacitance of the dielectric. Some polymers have excellent insulating properties, rated better than glass as dielectrics. However, glass can be the ultimate insulator because it can be drawn nearly flaw free. When the glass is nearly perfect it is the optimum dielectric material for a miniature HV cable. If glass is used, sealing of the glass to the conductors is critical. In the present invention described below, glass is used as a primary insulator in several embodiments, but the use of polymers is also disclosed in several embodiments.

At the cathode end of the x-ray tube, the HV cable must be connected in a way that is rugged, that does not greatly reduce flexibility of the device so as to be capable of travel through a tight design radius, and in a way that makes effective connections of the HV conductors, including the ground, without introducing conditions that would promote arcing and breakdown.

Solutions to these problems are the subject matter of the current invention described below.

SUMMARY OF THE INVENTION

In a miniature x-ray tube, on the order of approximately 1–4 mm in diameter, preferably 2 mm or 1 mm or even less, a high voltage cable is provided in various embodiments for conducting current and high voltages to the cathode of the x-ray tube and for providing ground to anode of the tube. For many radiation procedures in patient lumens or tissue, the cable must have sufficient flexibility to pass through tight curves. In preferred embodiments the cable of the invention can pass through curves having radius at least as small as 10 times the outside diameter of the cable preferably about 8 times the OD.

In various embodiments of the cable, at least two conductors occupy a center region of the cable, packed as closely together as possible, in various shapes that are compact and present as smooth as possible an external shape for maximizing dielectric properties against the exterior high voltage ground, surrounding and generally concentric with the inner conductors. The inner conductors, which carry high voltage in opposition to the outer ground, can be in opposed D shapes, coaxial, two flattened conductors side by side, or simply a pair of cylindrical wires positioned as closely as possible. The space between the inner conductors and the outer ground can be occupied by a glass insulator, a mixture of polymers and dielectric fillers, polymer, successive layers of polymers and adhesive, air, gas, vacuum or other dielectrics.

If the dielectric is loaded so that it is a semiconductor, and a nominal amount of current is allowed to flow between the conductors, the voltage gradient that is established will be due to the resistive divider rather than the capacitance of the insulator material. When a flaw is present that might defeat part of the dielectric withstand of the insulator, the resistive divider will work to smooth out the voltage distribution due to the parallel nature of the linear resistor.

Polymers are traditionally used to electrically insulate conductors in a cable from each other and from external influences. However, because of the nature of the x-ray tube and its requirements to be capable of sustaining high vacuum and bake out temperature environments, polymer seals on the x-ray tube are not possible. An alternative to insulating conductors with the polymers is to insulate them with glass. While glass provides an effective electrical insulation, it is susceptible to fracture at low stress levels unless protected. When protection is applied at the time of insulating glass manufacture, strength of the glass is up to 100 times that typically observed. This high initial strength can be preserved through the application of surface protective coatings onto the glass. This technology is utilized in the manufacture of fiber optic cables to allow fibers to tolerate the high stresses that occur during fiber bending and handling. Herein, the concept of surface protection of glass insulated metallic conductors is disclosed.

To be effective the seal between the metal conductors and the glass insulator must be good enough as to not compromise the vacuum integrity of the x-ray tube device. Also at all locations the seal between the metal conductors and glass must be adequate to avoid HV corona breakdown at the interface. These are considerations in the choice of materials, configuration and construction of the HV cables.

It is thus an object of the invention to provide efficient HV cables in very small diameters, in some embodiments not larger than about 4 mm and in some embodiments down to about 1 mm or even less, the cables exhibiting ruggedness, reliability, high dielectric strength and the ability to turn about tight radii. These and other objects, advantages and features of the invention will be apparent from the following description of a preferred embodiment, considered along with the accompanying drawings.

DESCRIPTION OF PREFERRED EMBODIMENTS

Figure 1:
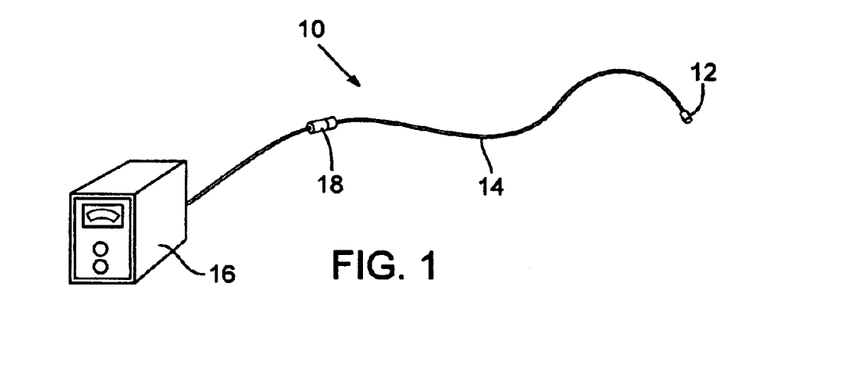
FIG. 1 is a view showing a high voltage cable of the invention connected to an x-ray source at its distal end, and indicating a control unit.

In the drawings, FIG. 1 shows schematically a system 10 according to the invention for administering x-rays using a switchable x-ray source. The system includes a miniature x-ray source 12 at the distal end of a cable 14, connected to a controller 16. The cable and x-ray source 14, 12 have important uses inside the human body, for various purposes discussed above. A connector 18 preferably is included, at a position which will remain outside a patient's body.

The cable 14 leading to the x-ray source 12 carries high voltage potential, up to about 50–60 kV, as well as carrying a low voltage cathode filament heater circuit. The low voltage conductors preferably also carry high voltage potential. The construction of such a cable, which must be small in diameter, flexible to travel around tight-radius curves and having a high dielectric property so as to resist breakdown, is the primary subject of the remaining drawings and of the discussion below.

Figure 2:
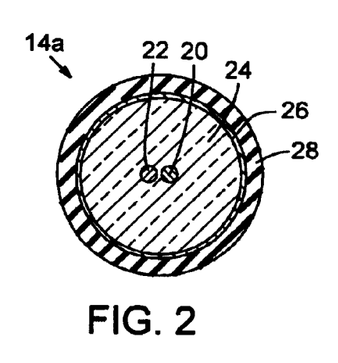
FIG. 2 is a schematic cross-sectional view showing one embodiment of the high voltage cable, with a pair of spaced apart, generally cylindrical conductor wires as inner conductors.

FIG. 2 shows one embodiment of a high voltage cable 14. The cable 14 has a pair of inner conductors 20 and 22, which in this embodiment are positioned side by side and spaced apart so as not to short the low voltage carried by these two inner conductors for heating the cathode. The two inner conductors 20, 22 may be held in position appropriately while being clad with a resistive dielectric 24 surrounding the inner conductors. On the outside of this resistive dielectric 24 is an outer, coaxial conductor 26 which carries high voltage ground potential.

If the resistive dielectric 24 is glass, it is most preferably nearly flaw free drawn glass, preferably fiber optic quality.

As an alternative, the dielectric material 24 can comprise a polymer material of high dielectric strength. Such insulating polymers can be effective for this purpose, but generally are not as effective as nearly-pure drawn glass, and may require a larger overall diameter in order to achieve sufficient separation between inner conductors and the outer conductor to prevent arcing and breakdown.

In the assembly of FIG. 2, the two inner conductors may be coated with a thin layer of insulation, or only one of the conductors may be so coated, and the two conductors may then be in contact. Otherwise, the two conductors 20 and 22 are held in a slightly spaced apart relationship as they are assembled with the insulation 24.

The ground layer 26 just outside the dielectric 24 can be made up of many very small diameter conductors, wrapped in a spiral or in a braid pattern around the dielectric. Alternatively, this ground can be formed of a conductive metallic material which is sputtered or evaporative coated onto the outside surface of the dielectric 24.

A jacket layer 28 is shown surrounding the ground layer 26 on the cable 14.

Figure 3:
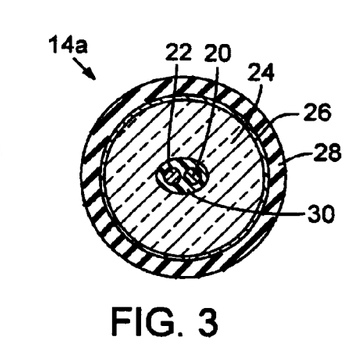
FIG. 3 is a cross-sectional view similar to FIG. 2 with conductors similar to FIG. 2 but including a resistive/partially conductive coating or composite over the two inner conductors.

FIG. 3 shows a modified high voltage cable construction. The modified cable 14a has construction similar to that of FIG. 2 with a pair of inner conductors 20 and 22, but in this case the inner conductors, one or both of which may have a thin insulated coating, are together covered with a resistive/partially conductive coating 30. The layer 30 is in a circular or slightly oval or elliptical shape and helps avoid breakdown in a very small cable carrying high voltage leading to the miniature x-ray tube. The coating 30 enshrouding the conductors 20 and 22 can have two advantages. First, this presents a smooth and round, circular or nearly-circular transition as an interface where arcing from the high potential must be held off from the opposing HV conductor, the ground 26. Arcing is more likely to occur if the inner HV conductors present an irregular surface toward the outer ground. Second, there is advantage to having a field-softening transition between the central area, where the cathode heater wires are located, and the outer ground.

The dielectric strength of the insulator in the cable has some intrinsic breakdown voltage and if the gradient across it is uniform and is very near that breakdown voltage, the cable is being used to its maximum or optimized extent. If the actual gradient between the high voltage center conductor and the ground is not uniform, then wherever it is higher than the average it potentially will break down that dielectric causing a cascade of voltage breakdown which will cause the cable to fail. So, rather than allowing the very high resistivity of the material—something typically on the order of $10^{15}$ ohm-cm for these materials—to define the gradient, if one puts a dopant in the dielectric it allows the cable to be somewhat lossy, especially around the center. This will establish a desired gradient and thereby insure that the gradient is always optimized.

Thus, the dielectric 24 is loaded so that it becomes a semi-conductor in the inner region 30 surrounding the center conductors, and a nominal amount of current is allowed to flow between the center conductors, assuming neither of them has an insulative coating. The voltage gradient that is established will be due to the resistive divider rather than the capacitance of the insulator material. When a flaw is present that might defeat part of the dielectric withstand of the insulator 24 the resistive divider will work to smooth out the voltage distribution due to the transition and due to the parallel nature of the linear resistor.

The only negative effect of this resistive/partially conductive coating or region theory is that the cable becomes somewhat lossy, and some power is dissipated in the cable, as a small amount of heat. This can be extremely small compared to the power that is put through the cable and thus is a reasonable tradeoff for the cable's not being perfectly insulated.

In a similar geometric approach to FIG. 3, conductors 20 and 22 may be insulated to prevent any substantial resistive divider network to develop. In this case the resistive region 30 is made up of a polymer/conductor or polymer/semi-conductor or a glass/conductor or a glass/semi-conductor such that the composite acts as a semi-conductor. By selection of the semi-condcutor additive, AC field absorbing attributes can be developed which results in an advantage that allows the cable to better tolerate transient changes (for example, caused by arcs in the x-ray source) that occur during operation. Both carbon conductors and ferrite semi-conductors are useful in this regard.

In FIG. 3, the resistive/partially conductive coating or region 30, which masks the non-circular symmetry of the center conductors can be consistent in resistivity/conductivity throughout the region 30 where it is present, with an abrupt change to the very high resistance of the dielectric insulative material 24, or it can be in a diminishing gradient outward from the center. In the latter case, the conductivity tapers off gradually, due to any distribution of dopant in the insulator diminishing with increasing radius, and this can continue all the way to the outer ground 26. This eliminates any hard boundary and may have the effect of eliminating any sharp wall from which breakdown could occur.

Figure 4:
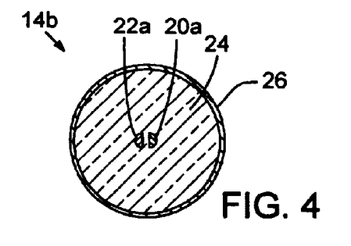
FIG. 4 is another cross-sectional view similar to FIG. 2, and showing a pair of back-to-back D-shaped conductors as the inner conductors.

FIG. 4 shows in cross section another HV cable construction, in this case with inner conductors 20a and 22a being back to back D-shaped conductors as shown. Again, the goals are to present a smooth surface at the composite high-voltage carrier and to make the pair of conductors together as small as possible, leaving more distance for dielectric material 24 between these center conductors and the outer ground 26. The two D-shaped conductors, if separated by a very thin insulator, present a nearly cylindrical surface toward the ground. The remaining construction of the cable 14b of FIG. 4 can be, as in FIG. 2, with the outer jacket (not shown) and with a high dielectric polymer as the insulative material 24, or more preferably, nearly perfect drawn glass as the insulator 24.

Figure 5:
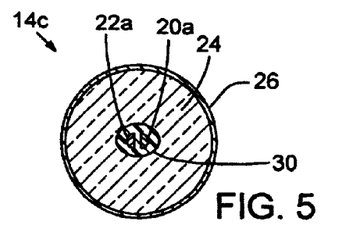
FIG. 5 is a view similar to FIG. 4 and with similar conductors, but including a resistive/partially conductive coating or composite over the inner conductors.

In FIG. 5, a HV cable 14c is similar to the cable 14b of FIG. 4, but in this case a resistive/partially conductive coating or region 30a is included surrounding the D-shaped center conductors 20a and 22a. Thus, the cable 14c gains the advantages discussed above relative to the constructions of both FIGS. 3 and 4 and can be even more effective in preventing breakdown.

Figure 6:
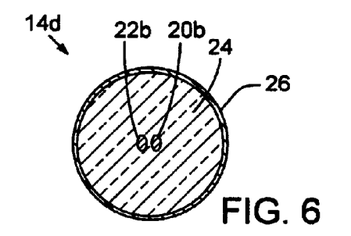
FIG. 6 is another cross-sectional view showing a high voltage cable, in this case with flattened conductors each of elongated cross-section.

In FIG. 6 partially flattened center conductors 20b and 22b are shown, in an HV cable 14d. The two flattened conductors, which can be rolled cylindrical conductors to the flattened shape, again make compact the pair of center conductors, in a simple and easily executed configuration. The conductors 20b and 22b can be spaced apart slightly or one or both can have a thin coat of insulation, holding off the low differential voltage required for cathode heating. As in the previous embodiments described above, the ground 26 at the outer surface of the dielectric 24 can be formed by dipping the formed cable with dielectric 24 into molten metal, such as aluminum. It can also be formed as a braided sheet of very small wires, or by helical wrapping of wires, preferably in two counter-directions.

Figure 7:
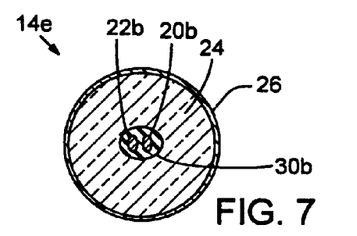
FIG. 7 is a cross-sectional view similar to FIG. 6, and with similar inner conductors, but with a resistive/partially conductive coating or composite over the inner conductors.

FIG. 7 shows a modification of the construction of FIG. 6 in which an HV cable 14e has flattened center conductors 20b, 22b that are coated with a resistive/partially conductive coating 30b, as in FIGS. 3 and 5, and with similar advantages.

Figure 8:
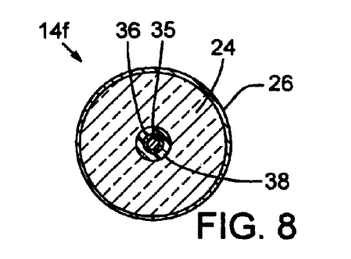
FIG. 8 is a cross-sectional view of a high voltage cable, in this embodiment showing a pair of inner conductors that are coaxial.

In FIG. 8, a HV cable 14f has a coaxial pair of inner conductors 35 and 36. This can be an optimal design for presenting a smooth surface of the inner conductors collectively to the outer ground 26, as an efficient design for holding off arcing and breakdown. The two conductors 35 and 36 may be closer together than what is represented in the not-to-scale drawings, the only requirement being a thin layer of insulation 38 between center conductor 35 and the coaxially arranged second conductor 36 surrounding the inner conductor. Such insulation layer 38 can be of a polymer or glass material.

Figure 9:
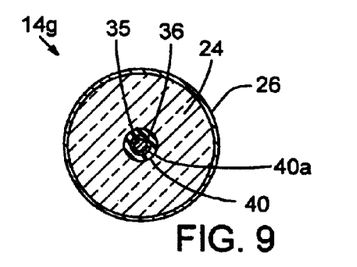
FIG. 9 is a cross-sectional view showing coaxial inner conductors in accordance with another embodiment, in this case with the inner conductor having insulative coating and the outer conductor comprising a further coating of partially resistive material.

FIG. 9 is another cross-sectional view that schematically indicates a further form of HV cable 14g. In this case, the inner conductors 35 and 36 again are coaxial, but the assembly includes an outer layer 40 of resistive/partially conductive material 40 generally as was applied in FIGS. 3, 5 and 7. Again, as in FIGS. 3, 5 and 7, this layer 40 can have a sharply defined boundary 40a or it can be on a gradient, from most conductive adjacent to the coaxial conductor 36 to least conductive and very highly resistive at a location such as shown at 40a, or extending substantially entirely out to the ground 26. This particular construction provides essentially a maximum protection against breakdown in the cable.

Figure 10:
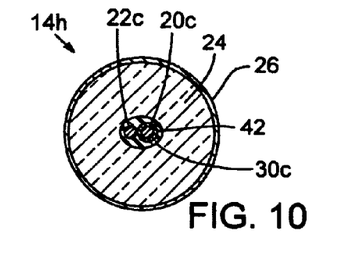
FIG. 10 is a cross-sectional view schematically showing another embodiment of a high voltage cable, in this case with two generally cylindrical and spaced apart inner conductors as in FIG. 3, with a resistive/partially conductive coating or composite around the conductors, but in this case with an insulative coating over one of the inner conductors.

FIG. 10 shows another embodiment of a HV cable 14h, in this case with two generally cylindrical and spaced apart inner conductors 20c and 22c as in FIG. 3, and with a resistive/partially conductive coating 30c surrounding the two inner conductors. In this case an insulative coating 42, which may be of glass, surrounds one inner conductor 20c (the drawings are not to scale). The two inner conductors 20c and 22c can thus be held tightly together with one of them insulated. The resistive/partially conductive coating 30c may be as described above with respect to other embodiments.

It should be understood that in all embodiments described above, the dielectric material 24 can be a polymer material with very good insulative properties, rather than glass. However, in general the smaller the outside diameter of the HV cable, the more it becomes important to use a nearly perfect drawn glass as the dielectric 24, for maximum withstand properties.

In the event a resistive/partially conductive layer or region is included surrounding the inner conductors, as in FIGS. 3, 5, 7, 9 and 10 as described above, this layer or region can be formed in various ways. One way is to dope the center region with semiconductive particles such as titanium or an oxide of titanium (oxidation may occur during processing) when the glass is in a molten state, form the insulator around the inner conductive wires, whether this is done by drawing a glass preform on the wires or by providing a glass tube within which the wires are placed, and then filled under vacuum with a low viscosity curable material (such as by light). With the doping material in place, the partially conductive region can have a fixed boundary at a particular radius, or it can be heated to the point of flowing so as to fuse the glass and cause the doping to spread outwardly, forming the gradient-placed conductive material which is advantageous as discussed above. Alternatively, multiple layers can be assembled, each having different resistance. The resistive/partially conductive layer or region can be extruded, with the conductors captured in the extrusion. If desired to establish a gradient of conductivity, layers of extrusion can be formed successively, each with less conductive doping. If desired the composite structure could then later be heated to fuse the layers together.

As reviewed above, the dielectric material surrounding the inner conductors can take several forms, and can be assembled onto the conductors in several different ways. Generally, the smaller the diameter (e.g. down to 1 mm or even down to about 0.5 mm) the more it becomes necessary to use drawn glass substantially of fiber optic quality, which is nearly perfect and is an excellent dielectric. Nonetheless, various methods and materials for constructing a small HV cable are discussed below.

One method is to use a glass tubing into which the conductors are inserted. The conductors can be overcoated with a polymer before insertion to prevent damage to the glass tube inside surface, and they can be potted into the glass tubing internal diameter with a dielectric polymer such as one of several silicone products. The conductors could be pre-overcoated with glass, followed by a polymer overcoat, and then with a polymer potting the coated conductors into the interior of the glass tube.

In another method of fabrication, glass is drawn around the metallic conductors. The metallic conductors can be bare, and held apart appropriately, or more preferably, the metallic conductors, or one of them, can be precoated with a glass coating. The inclusion of a thin insulative coating on one of the conductors allows the conductors to be placed tightly and compactly together within the insulator surrounding the conductors. Various glasses have been investigated and developed to allow a heat seal to be successfully made between the HV cable and the x-ray tube envelope (shown schematically at 12 in FIG. 1). These include silica glass clad with polymer; silica glass clad with aluminum; borosilicate glass (e.g. from Corning), either as tubing within which the conductors are placed, or with the glass drawn around the conductors; and alumino silicate glass (e.g. Schott 8250 or 8253 or Kimble N51A), drawn around conductors. The cladding acts as a buffer to protect the essentially fiber optic quality glass which otherwise will begin to degrade by developing surface micro cracking very quickly after drawing, if the buffer is not added to protect the surface. These glass types can be used with any of the disclosed embodiments in FIGS. 2 through 10.

Figure 11:
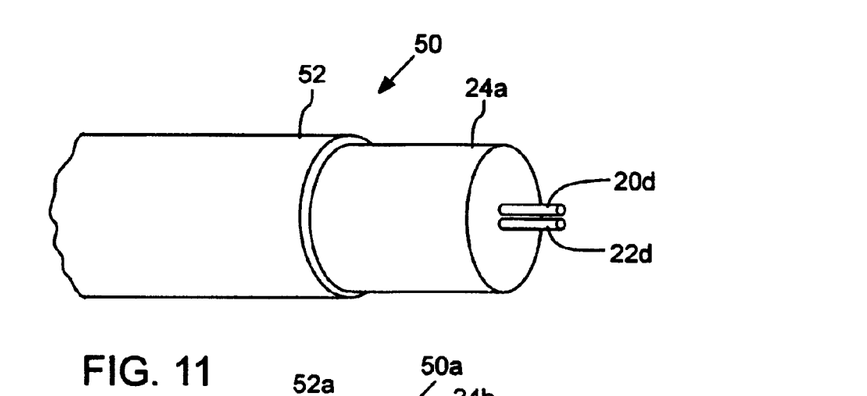
FIGS. 11 and 12 are similar perspective views showing high voltage cables formed of clad glass insulated wires in somewhat modified embodiments.
Figure 12:
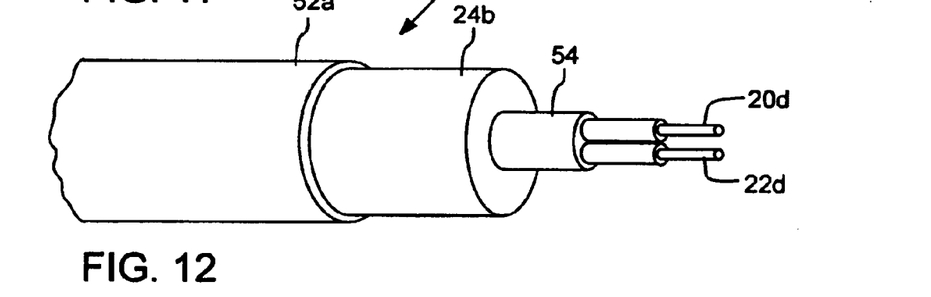

FIGS. 11 and 12 show in perspective two different examples of clad glass insulated inner conductive wires in an HV cable. In FIG. 11 an HV cable 50 has a pair of conductors 20d, 22d that are shown spaced apart but which can actually be very close together. In this case they are shown not individually coated with insulation, although one or both can be clad with an insulative material such as glass. Preferred materials for the conductors are molybdenum, tungsten, or gold/palladium/platinum clad versions. The wires can also be niobium or osmium, or similarly clad versions of these materials. Glass insulation is shown at 24a, surrounding the 2 conductors 20d and 22d. Fabrication and material can be by the various techniques described above.

As discussed above, a metal or polymer protective cladding 52 is secured on the outside of the insulator 24a. This protective cladding can be, for example, any of the metals aluminum, nickel, gold, platinum or palladium or alloys thereof. Polymers for this purpose include polyimide. Surrounding this protective cladding, if the cladding is of an insulative material such as polymer, will be the ground conductor (not shown). The ground conductor is indicated at 26 in some of the drawings discussed above. As discussed earlier, it can be formed of fine braided wire or fine wires wrapped helically around the cladding and repeated in the opposite direction, covering almost the entire surface; or the ground could be solid metal, deposited as by coating or plating.

In FIG. 12 a variation is shown of the construction in FIG. 11. Here, the metallic conductors 20d, 22d are first covered with insulation, or preferably only one of them is covered with insulation. This can be a glass cladding, very thin, and the conductors can then be positioned tightly together. If desired, the cladding can be a polymer, since the assembly will not be heated to a high temperature. The insulator 24b in this case is a pre-formed tube as discussed above, within which the metallic conductors 20d, 22d are placed, and are potted therein with an infiltrated polymer dielectric 54. The dielectric 54 is added by squeezing it in after the wires are inserted. The polymer chosen must wet the surfaces to exclude adherent air bubbles. A vacuum can be used to remove air prior to adding the polymer dielectric.

At the outside of the glass insulation tube 24b in the HV cable 50a is a metal or polymer cladding 52a, which can be configured and constructed as discussed above relative to FIG. 11. Again, if the cladding is non-conductive, then a braided or other type of ground is placed around the outside of the cladding 52a. As an alternative, a metal coating can be applied for the ground, as by dipping or drawing the cable into or through a molten bath of metal.

As outlined above, high dielectric polymers can be used as the insulator in many cases. One method of preparing the cable is to co-extrude the inner conductors with the polymer insulation. The insulating material must surround and encapsulate the high voltage (inner) conductors, with minimized voids between the inner conductors and the insulating material. Co-extrusion can accomplish this purpose. The inner conductors are small gauge metal wires, which may be about 33 gauge or smaller. The inner conductors are sent through a circular extrusion die and are surrounded by molten polymer. In a similar way, the extrusion can be accomplished in two steps for cables with semi-conductive inner layers like those shown in FIG. 3. The inner layer polymer would contain semi-conductive additives, where the outer layer would act as the HV dielectric. In either case, following extrusion, the polymer and conductor assembly is cooled and hardens to a solid state, leaving virtually no gaps or voids between the inner conductors and the insulation. This assembly can withstand a high voltage as is contemplated by the invention (50 kV or higher), provided the outer diameter of the cable is not too small. This assembly works well for outer diameters of about 3 mm. In one specific embodiment the OD of the polymer is about 2.2 mm and OD of the cable is about 3.2 mm, in a 50 kV cable.

Figure 13:
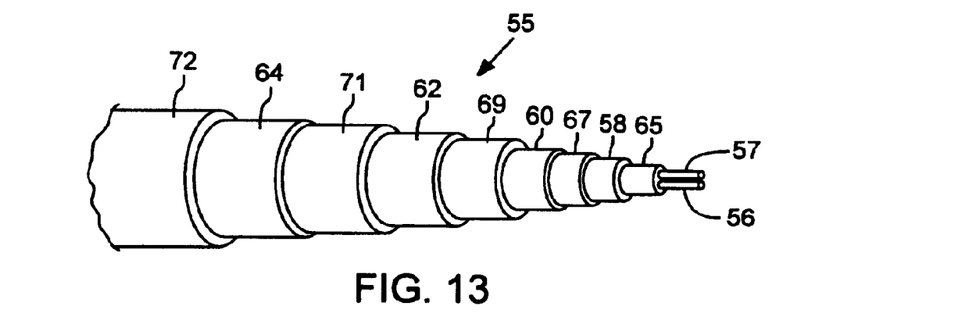
FIG. 13 is a perspective view showing a high voltage cable construction with multiple layers of polymer and adhesive.

FIG. 13 shows in perspective an alternative construction for an HV cable 55. Here, a pair of conductors 56 and 57, shown spaced apart but preferably with at least one of the conductor wires pre-coated with a high dielectric polymer material, are shown at the center of the HV cable assembly. In this case the insulator for the cable is formed of a series of layers of TEFLON grade heat shrink material, and adhesive. Shown schematically (not to scale) at 58, 60, 62, and 64 are layers of TEFLON grade heat shrink material. These layers, as the name implies, are applied by heat shrinking them onto the previous layer. Shown at 65, 67, 69 and 71 are adhesive layers, preferably a high dielectric silicon material. The outer layer 72 indicates further layers as desired.

The adhesive/silicon layers provide for HV creep and bond the layers together substantially without voids. The TEFLON grade heat shrink can be the same material or different heat shrink materials in different layers. These multiple layers provide for high dielectric withstand; minimize effects of any localized defects on the heat shrink layers by offsetting them using the layering format; and provide optimum electric field control by carefully choosing the desired combination of different grades of heat shrink materials. When adhesive is used between layers of heat shrink to remove trapped air pockets, the heat shrink tubing is chemically etched or plasma etched to increase the bondability of the plastic surface. In some cases, silicon layers applied between the heat shrink layers will provide high voltage creep resistance as noted above. Choosing the adequate heat shrink material is important. Some preferred materials are high quality FEP and/or PFA, both being TEFLON grade. Certain heat shrink FEP polymers were specially processed to rid them of insoluble particulate impurities to reduce the tendency of internal corona formation during high voltage stress. The construction shown in FIG. 13 can be effective down to about 2 mm OD of the outer layer 72.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A high voltage cable for a miniature x-ray source, for carrying high voltage potential for a cathode and an anode of the source and also for carrying current for a low voltage cathode heating circuit, comprising:

the cable having an outside diameter not larger than about 4 mm, the cable having two inner conductors and an outer conductor, and carrying a voltage greater than about 10 kV between the inner conductors and the outer conductor, the inner conductors being electrically isolated from one another and also carrying a low differential voltage cathode filament heater current, including a dielectric material insulating the inner conductors from the outer conductor, and the conductors and the dielectric material being of sufficient flexibility such that the cable can pass through curves having a radius of curvature at least as small as about 8 times the outside diameter of the cable.

2. A high voltage cable according to claim 1 wherein the outside diameter of the cable is at least as small as about 1 mm.

3. A high voltage cable according to claim 1 wherein the outside diameter of the cable is at least as small as about 0.5 mm.

4. A high voltage cable according to claim 1 wherein the voltage carried in the cable is at least about 20 kV.

5. A high voltage cable according to claim 1 wherein the voltage carried in the cable is at least about 40 kV.

6. A high voltage cable according to claim 1 wherein the voltage carried in the cable is at least about 50 kV.

7. A high voltage cable according to claim 1, wherein the conductors and the dielectric material are of sufficient flexibility that the cable can pass through curves having radius of curvature at least as small as about 5 times the outside diameter of the cable.

8. A high voltage cable according to claim 1, wherein the outer diameter of the cable is about 3 mm and the cable is of sufficient flexibility to pass through curves having a radius of curvature at least as small as about 20 mm.

9. A high voltage cable according to claim 1, wherein the dielectric material comprises drawn glass substantially of fiber optic quality.

10. A high voltage cable according to claim 1, wherein the inner conductors are spaced apart and surrounded by the dielectric material, including between the inner conductors.

11. A high voltage cable according to claim 10, wherein the dielectric is a polymer material.

12. A high voltage cable according to claim 1, wherein one of the two inner conductors is coated with an insulative coating, the two conductors being essentially in contact but separated by the insulative coating and the conductors being generally round in cross section.

13. A high voltage cable according to claim 12, wherein said insulative coating comprises glass, and wherein the dielectric material comprises drawn glass substantially of fiber optic quality.

14. A high voltage cable according to claim 13, wherein the glass dielectric has been drawn into contact with the two inner conductors.

15. A high voltage cable according to claim 13, wherein the glass dielectric insulator comprises a glass tube and wherein the two conductors are within the inner diameter of the glass tube and are packed therein with a dielectric potting material.

16. A high voltage cable according to claim 13, further including in the glass dielectric material a resistive/partially conductive region around the conductors, with a substantially cylindrical configuration at an outer diameter of the region, to improve the dielectric characteristics of the cable.

17. A high voltage cable according to claim 13, further including a resistive/partially conductive region surrounding the inner conductors, comprising a conductive doping in the glass insulation, the doping being in a graded pattern such that with increasing radius conductivity is reduced, substantially to zero at the outside diameter of the glass insulator.

18. A high voltage cable according to claim 1, wherein one of the two inner conductors is coated with an insulative coating, the two conductors being essentially in contact but separated by the insulative coating and the inner conductors being generally D-shaped and side-by-side and close together so as to present a substantially round outer surface of the two inner conductors to improve dielectric strength of the cable.

19. A high voltage cable according to claim 18, wherein one of the D-shaped inner conductors is pre-coated with an insulative coating and the inner conductors are very close together, essentially in contact.

20. A high voltage cable according to claim 18, further including in the glass dielectric material a resistive/partially conductive region around the conductors, with a substantially cylindrical configuration at an outer diameter of the region, to improve the dielectric characteristics of the cable.

21. A high voltage cable accordingly to claim 18, further including a resistive/partially conductive region surrounding the inner conductors, comprising a conductive doping in the glass insulation, the doping being in a graded pattern such that with increasing radius conductivity is reduced, substantially to zero at the outside diameter of the glass insulator.

22. A high voltage cable according to claim 1, wherein the two inner conductors are each flattened, generally oval or elliptical in shape, one of the two conductors being pre-coated with an insulative coating.

23. A high voltage cable according to claim 22, wherein said insulative coating comprises glass, and wherein the dielectric material comprises drawn glass substantially of fiber optic quality.

24. A high voltage cable according to claim 23, further including in the glass dielectric material a resistive/partially conductive region around the inner conductors, with a substantially cylindrical configuration at an outer diameter of the region, to improve the dielectric characteristics of the cable.

25. A high voltage cable according to claim 23, further including a resistive/partially conductive region surrounding the inner conductors, comprising a conductive doping in the glass insulation, the doping being in a graded pattern such that with increasing radius conductivity is reduced, substantially to zero at the outside diameter of the glass insulator.

26. A high voltage cable according to claim 1, wherein the two inner conductors are coaxial.

27. A high voltage cable according to claim 26, wherein the dielectric material comprises a polymer.

28. A high voltage cable according to claim 26, wherein the dielectric material comprises drawn glass substantially of fiber optic quality.

29. A high voltage cable according to claim 28, further including in the glass dielectric material a resistive/partially conductive region around the conductors, with a substantially cylindrical configuration at an outer diameter of the region, to improve the dielectric characteristics of the cable.

30. A high voltage cable according to claim 28, further including a resistive/partially conductive region surrounding the inner conductors, comprising a conductive doping in the glass insulation, the doping being in a graded pattern such that with increasing radius conductivity is reduced, substantially to zero at the outside diameter of the glass insulator.

31. A high voltage cable according to claim 1, wherein the dielectric material is coextruded with the inner conductors.

32. A high voltage cable according to claim 1, wherein at least one of the two inner conductors is pre-coated with insulative coating and the two inner conductors are nested closely together, and wherein the inner conductors are co-extruded with PFA polymer, by extruding the PFA material over the conductors such that essentially no residual entrained air remains between the conductors and the PFA material, the PFA material serving as the dielectric material or insulator, wherein said outer conductor is a ground and comprises a braided or wrapped series of conductive wires covering most of the outer surface of the PFA insulator, and including a protective jacket covering the ground conductor.

33. A high voltage cable according to claim 32, wherein the ground conductor comprises wires helically wound in two opposite directions around an outer surface of the PFA insulator.

34. A high voltage cable according to claim 32, wherein the protective outer jacket of the high voltage cable comprises FEP or urethane material.

35. A high voltage cable according to claim 32, wherein the protective outer jacket of the high voltage cable comprises a TEFLON class material.

36. A high voltage cable according to claim 32, wherein the outer diameter of the cable, including the protective jacket, is about 3.2 mm.

37. A high voltage cable according to claim 36, wherein the heat shrink material comprises a TEFLON grade heat shrink material.

38. A high voltage cable according to claim 36, including at least four layers of adhesive and four layers of heat shrink material.

39. A high voltage cable according to claim 1, wherein the dielectric is a polymer material, and including in the polymer dielectric material a resistive/partially conductive region around the conductors, with a substantially cylindrical configuration at an outer diameter of the region, to improve the dielectric characteristics of the cable.

40. A high voltage cable according to claim 1, wherein the dielectric material insulating the inner conductors from the outer conductors comprises a series of layers of polymer materials surrounding the inner conductors, comprising alternating layers of heat shrink material.

41. A high voltage cable for a miniature x-ray source, for carrying high voltage potential for a cathode of the source and also for carrying a low differential voltage cathode heating current, comprising:

the cable an outside diameter not larger than about 3 mm,
the cable having two inner conductors and an outer conductor and carrying a voltage greater than about 40 kV between the inner conductors and the outer conductor,
the inner conductors being electrically isolated from one another and also carrying a low differential voltage cathode filament heater current,
a dielectric material isolating the inner conductors from the outer conductor to prevent arcing and breakdown, the dielectric material comprising drawn glass substantially of fiber optic quality, and
the conductors and the dielectric material being of sufficient flexibility such that the cable can pass through curves having a radius of curvature at least as small as about 10 times the outside diameter of the cable.

42. A high voltage cable according to claim 41, wherein the outer diameter is at least as small as about 1 mm.

43. A high voltage cable according to claim 41, wherein the voltage carried in the cable is at least about 50 kV.

44. A high voltage cable according to claim 41, wherein the conductors and the dielectric material are of sufficient flexibility that the cable can pass through curves having radius of curvature at least as small as about 5 times the outside diameter of the cable.

45. A high voltage cable according claim 44, wherein the outside diameter of the cable is at least as small as about 1 mm.

* * * * *